United States Patent [19]

Fullington et al.

[11] 4,099,005

[45] Jul. 4, 1978

[54] APPARATUS AND METHOD FOR DISPENSING SOLIDS INTO A LIQUID MEDIUM

[75] Inventors: Michael C. Fullington; Kurt H. Moller, both of Lake Charles, La.

[73] Assignee: Olin Corporation, New Haven, Conn.

[21] Appl. No.: 782,677

[22] Filed: Mar. 30, 1977

[51] Int. Cl.$^2$ .................. C07D 251/31; C07D 251/36
[52] U.S. Cl. ................................. 544/190; 252/363.5; 544/192
[58] Field of Search .......................................... 544/190

Primary Examiner—John M. Ford
Attorney, Agent, or Firm—Bruce E. Burdick; Donald F. Clements; Thomas P. O'Day

[57] ABSTRACT

A device for dispensing solid into a liquid medium. The device utilizes a funnel with a vortical stream therein for feeding solids into a reaction zone. A portion of the contents of the reaction zone are recycled to supply the fluid for the vortical stream. The device finds particular use in dispersing dry particulate blends of isocyanuric acid and trichloroisocyanuric acid into a reaction slurry.

8 Claims, 3 Drawing Figures

APPARATUS AND METHOD FOR DISPENSING SOLIDS INTO A LIQUID MEDIUM

This invention relates to material handling and more specifically to devices for dispersing solids into a liquid medium. "Vortical stream" as used herein shall mean a rapidly moving swirling, whirling or turbulent stream such as in a dentist bowl or flushing toilet bowl.

Some solids are notoriously difficult to handle because of their small size and tendency to become charged. Dry solids may resist flow over even small distances and extremely fine particulate solids may resist dispersion into a liquid medium because of their tendency to not wet. Such a problem can be encountered in the production of sodium dichloroisocyanurate.

One method of producing sodium dichloroisocyanurate (NaDCC) involves metering a very fine particulate blend of trichloroisocyanuric acid (TCCA) and isocyanuric acid (CA) into a reaction slurry. The solids would not fall freely through a glass pipe into a reactor for any extended length of time.

An object of this invention is to provide a device to disperse such solids into the reaction slurry.

This invention provides a method of continuously dispersing solids into a liquid medium in a continuous process for producing a product, said method comprising:
(a) continuously introducing a quantity of a liquid reactant into a reaction zone;
(b) continuously withdrawing a portion of the contents of said reaction zone;
(c) transferring a minor part of said withdrawn portion to a take-off zone;
(d) accelerating a major part of said withdrawn portion;
(e) continuously passing said accelerated major part in a vortical stream through said contact zone;
(f) continuously introducing a quantity of solids into a central portion of said vortical stream so as to mix said solids into said vortical stream, thereby preventing accumulation of said introduced solids within said contact zone; and
(g) continuously introducing said solid-mixed liquid stream to said reaction zone.

In another aspect, this invention provides an apparatus for continuously feeding solids into a reaction zone comprising:
(a) a reaction zone;
(b) liquid supply means for continuously introducing a quantity of liquid into said reaction zone;
(c) withdrawal means for continuously withdrawing a portion of said liquid from said reaction zone;
(d) acceleration means for accelerating a major part of said withdrawn portion;
(e) a contact zone;
(f) withdrawn liquid feed means for continuously passing said accelerated withdrawn portion in a vortical stream through said contact zone;
(g) solids supply means for continuously introducing a quantity of particulate solids into a central portion of said vortical stream, thereby producing a solids-liquid mixture; and
(h) mixed stream feed means for continuously transferring said solids-liquid mixture from said contact zone into said reaction zone.

In yet another aspect, this invention provides an apparatus for dispersing solids into a liquid medium, comprising,
(a) a vertical funnel having an inner surface;
(b) a splash guard atop said funnel;
(c) a liquid supply means, attached to said funnel, for producing a vortical liquid stream along said inner surface; and
(d) braking ridge means, lying along a major portion of said inner surface, for braking said vortical stream.

Also, in still another aspect this invention provides a system for dispersing a dry particulate blend of trichloroisocyanuric acid and isocyanuric acid into a reaction slurry in a reactor, said system comprising:
(a) a funnel having an inner surface;
(b) wash means for producing a vortical wash stream along said inner surface;
(c) liquid feed means for continuously introducing a liquid reactant into said reactor;
(d) solids feed means for continuously introducing said particulate blend into a central portion of said vortical stream so as to produce a slurry stream;
(e) slurry stream feed means connected to both said funnel and said reactor for tranferring said slurry stream from said funnel to said reactor; and
(f) slurry recycle means attached to both said reactor and said wash means for withdrawing a portion of the contents of said reactor and accelerate said contents and supplying said accelerated reactor contents to said wash means.

The invention is more fully described in the attached drawing, which describes a preferred embodiment by way of example and not by way of limitation, and in which.

Figure 1:
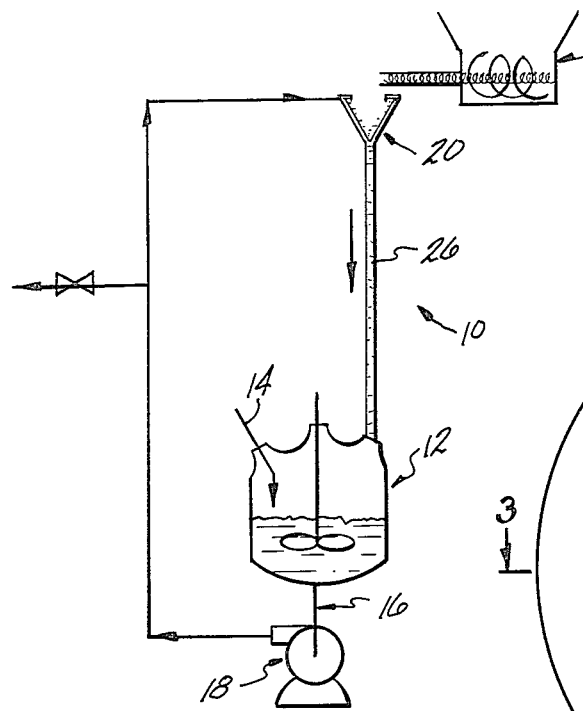
FIG. 1 is a schematic diagram of a preferred embodiment of a solid-liquid contacting device applied to a reactor.

FIG. 1 provides an overall schematic representation of a preferred embodiment of the invention and particularly shows a feed system 10 comprising a reaction zone 12, a liquid supply means 14, withdrawal means 16, acceleration means 18, contact zone 20, solids supply means 22, withdrawn liquid supply means 24, mixed stream feed means 26, take-off means 50 and take-off zone 52. Reaction zone 12 can be a chemical reactor for at least a portion of a chemical reaction to produce sodium dichloroisocyanurate. Reaction zone 12 could also be any conventional chemical reactor which requires a slurry which includes as one or more ingredients a material which is to be fed into the system 10 in dry particulate form. The particular ingredients for which the invention is best envisioned are TCCA, CA and a sodium hydroxide (NaOH) solution as utilized to make NaDCC. Liquid supply means 14 can be a sodium hydroxide (NaOH) solution or any suitable reaction liquid as desired that would be operative in connection with a desired reaction and can be fed into reaction zone 12 continuously at a predetermined rate. One GPM has been found to be a satisfactory rate. Withdrawal means 16 can be a gravity fed drain, a suction portion of a pump or any other means for continuously withdrawing a portion of the contents of reaction zone 12. Acceleration means 18 can be the discharge portion of a pump, a centrifuge or any other operable means for acceleration of the portion of the contents withdrawn by withdrawal means 16 from negligible velocity to a velocity sufficient to create an effective wash. A flow rate of 29 gallons per minute (GPM) was found sufficient for the wash stream and gave adequate velocity. A specific device which could serve as both withdrawal means 16 and accelerator means 18 is a rotating impeller type circulating pump of corrosion resistant construction so that operation is not prevented if the liquid supplied by liquid supply means 14 is corrosive or caustic, as is true when NaOH is the liquid supplied.

Solids supply means 22 can include any conventional means for supplying particulate solids such as a worm screw solids feeder, a pneumatic plenum solids conveying system, a conveyor belt or other means for continuously introducing a quantity of solids into a central portion of contact zone 20. A suitable rate of supply was found to be about 40 pounds per hour to produce a product slurry of about one GPM at take-off zone 52.

Withdrawn liquids feed means 24 can be a pipe, tube, nozzle or other conduit or trough or any suitable device for continuously passing a major portion of the accelerated withdrawn portion in a vortical stream through the contact zone 20. A suitable portion has been found to be 29 GPM recirculated out of 30 GPM withdrawn, the remaining 1 GPM being taken off from feed means 24 through take-off means 50 and passed to take-off zone 52 for further processing. Any desired amount could be taken off so long as the wash stream was sufficient.

Mixed stream feed means 26 can simply be a gravity fed glass feed tube from the bottom of contact zone 20 leading into the reaction zone 12 so that the passage of slurry therethrough may be visually observed or means 26 can be any other device suitable for continuously transferring a solids-liquid mixture from the contact zone 20 into the reaction zone 12.

Figure 2:
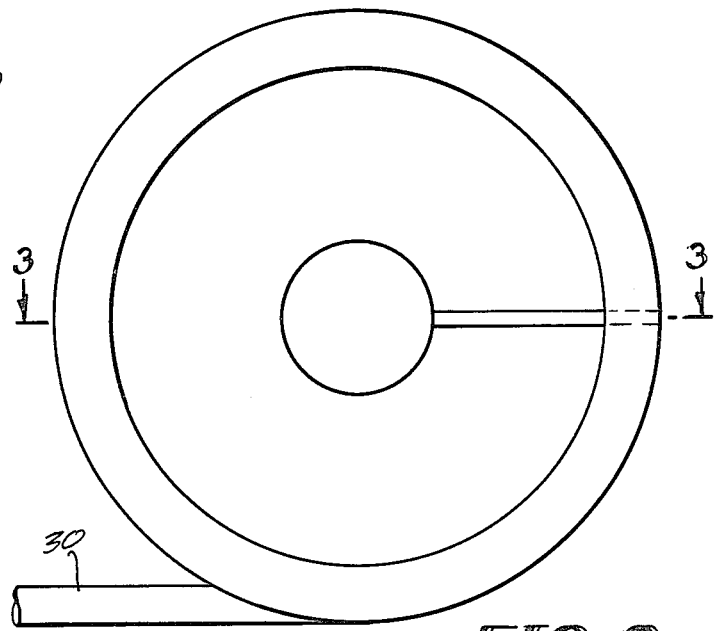
FIG. 2 is a top plan view of the solid-liquid contactor of FIG. 1 in a dry condition.
Figure 3:
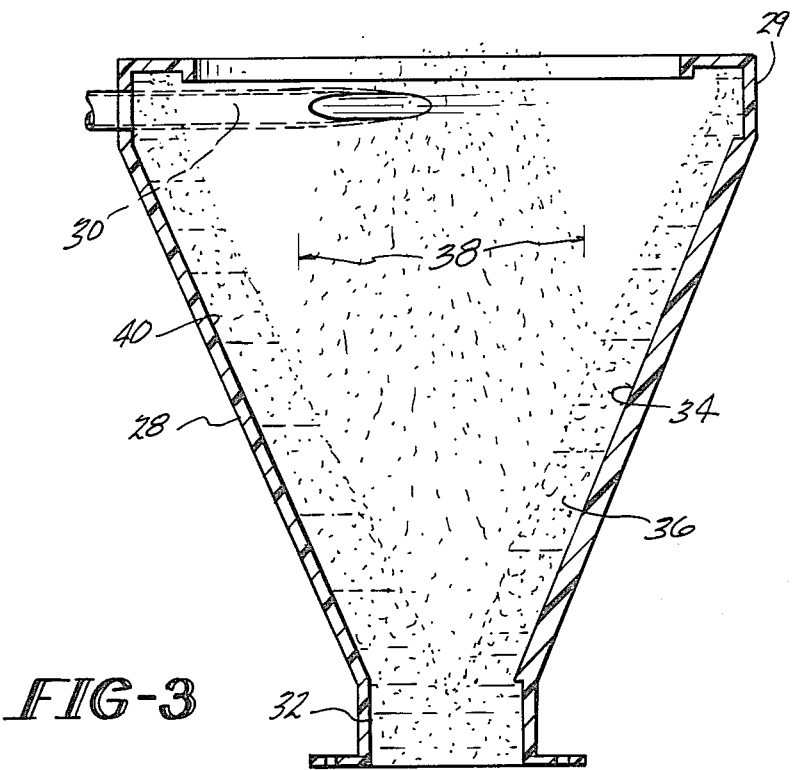
FIG. 3 is a side cross-sectional elevational view of the solid-liquid contactor of FIG. 2 in operation taken along lines 3—3 of FIG. 2.

The contact zone 20 is best described with reference to FIGS. 2 and 3 and is preferably an apparatus which comprises a funnel 28, a splash guard 29, a contact zone inlet means 30, an outlet 32 and a braking ridge 34. Funnel 28, splash guard 29, contact zone inlet means 30, outlet 32 and braking ridge 34 can be made as an integral unit out of molded fiberglass reinforced plastic suitable for corrosive ingredients such as may be present in the liquid utilized to create a vortical stream or any other suitable material. The vortical stream 36 produced by liquid exiting contact zone inlet means 30 serves to wash the solids introduced by solids supply means 22 into contact zone 20. A flow rate of about 29 GPM was found satisfactory. Solids are preferably introduced over a central portion 38 of contact zone 20 so that the vortical stream 36 is uniform at the point at which the solid contacts the stream 36. The vortical stream forms a rapidly moving liquid layer through which solids must pass in order to accumulate on the inner surface 40 of funnel 28. Also, vortical stream 36 serves to wet the solids and thereby reduce or eliminate any static electrical charge of said particles to help prevent interparticulate attraction within said solids. Thus a surprisingly uniform slurry is produced and this slurry exits through outlet 32 and preferably passes downwardly to the reaction zone 12 under the force of gravity. Braking ridge 34 serves to counteract the tendency of vortical stream 36 to accelerate as the stream 36 flows downwardly through the decreasing diameter of the funnel. Thus braking ridge 34 gives vortical stream 36 a more uniform thickness along the wall of the funnel and reduces the tendency of the stream to tend to rise in the funnel due to increasing centrifugal forces resulting from increased speed during unrestricted travel through the funnel.

EXAMPLE 1

In a process for the production of NaDCC from a TCCACA dry particulate blend metered into a NaOH solution, the rate of supply being about 1 gallon per minute of NaOH solution and about 40 pounds per hour of the TCCA-CA blend, a solids-liquid contactor was added at the top of the glass tube and a portion of the product of the reactor, which is a NaDCC slurry, was withdrawn from the reactor at a rate of about 30 GPM and 29 GPM were recirculated to the solids-liquid contactor to create a vortex wash which served to carry the TCCA-CA blend into the reactor. The remaining 1 GPM of NaDCC product was taken off or withdrawn from the process and fed to a take-off zone for further processing. The solids-liquid contactor was a funnel of fiberglass reinforced plastic having an 8 inch high cone of 8 inch diameter atop a 2 inch outlet pipe.

A 1 inch high by $\frac{3}{4}$ inch wide lip was placed atop the cone as a splash guard, and $\frac{3}{4}$ inch inlet pipe was tangentially attached to the cone top to create a vortical wash. A $\frac{1}{4}$ inch copper tube was placed in the funnel as a braking ridge.

The TCCA-CA blend was metered at up to 100 lbs./hr. into the reactor without any clogging of the 2 inch glass pipe. The wash was of about $\frac{3}{4}$ inch uniform depth along the wall of the solids-liquid contactor.

By way of comparison, a process for the production of NaDCC without the invention was practiced. A very fine, dry particulate blend of TCCA and CA was directly metered into the reactor through a 6 foot 2 inch ID glass tube at a rate of about 40 pounds per hour. The solids flowed poorly and on several occasions the glass tube became clogged with solids.

It will be readily apparent to those skilled in the art that other modifications could be made to the preferred embodiments shown within the scope of the invention, and the following claims are to be interpreted to cover all such equivalents.

What is claimed is:

1. A system for dispersing a dry particulate blend of trichloroisocyanuric acid and isocyanuric acid and a sodium hydroxide solution liquid reactant into a reaction slurry in a reactor to produce sodium dichloroisocyanurate, said system comprising:
   (a) a funnel having an inner surface;
   (b) wash means for producing a vortical wash stream along said inner surface;
   (c) liquid feed means for continuously introducing said liquid reactant into said reactor;
   (d) solids feed means for continuously introducing said particulate blend into a central portion of said vortical stream so as to produce a slurry stream;
   (e) slurry stream feed means connected to both said funnel and said reactor for transferring said slurry stream from said funnel to said reactor; and
   (f) slurry recycle means attached to both said reactor and said wash means for withdrawing a portion of the contents of said reactor and accelerating said contents and supplying said accelerated reactor contents to said wash means.

2. The apparatus of claim 1 wherein said liquid reactant is a solution comprising sodium hydroxide.

3. A method of continuously dispersing solids into a liquid medium in a continuous process for producing a product, said method comprising:
   (a) continuously introducing a quantity of a liquid reactant into a reaction zone;
   (b) continuously withdrawing a portion of the contents of said reaction zone;
   (c) transferring a minor part of said withdrawn portion to a take-off zone;
   (d) accelerating a major part of said withdrawn portion;
   (e) continuously passing said accelerated major part in a vortical stream through said contact zone;
   (f) continuously introducing a quantity of solids into a central portion of said vortical stream so as to mix said solids into said vortical stream, thereby preventing accumulation of said introduced solids within said contact zone;
   (g) continuously introducing said solid-mixed liquid stream to said reaction zone, and
   (h) said solids comprising trichloroisocyanuric acid and isocyanuric acid, said liquid reactant comprising a sodium hydroxide solution, and said product comprising sodium dichloroisocyanuric acid.

4. The method of claim 3 wherein:
   (a) said liquid reactant is a solution containing sodium hydroxide.

5. The method of claim 3, wherein said method further comprises the step of braking said vortical stream so as to achieve a more uniform stream velocity within said contact zone.

6. The method of claim 3 wherein:
   (a) said major part is more than 90 percent of said withdrawn portion; and
   (b) said minor part is less than 10 percent of said withdrawn portion.

7. Apparatus for continuously feeding a dry particulate blend of trichloroisocyanuric acid and isocyanuric acid into a reaction zone comprising:
   (a) a reaction zone;
   (b) liquid supply means for continuously introducing a quantity of sodium hydroxide solution liquid into said reaction zone;
   (c) withdrawal means for continuously withdrawing a portion of said liquid from said reaction zone;
   (d) acceleration means for accelerating a major part of said withdrawn portion;
   (e) a contact zone;
   (f) withdrawn liquid feed means for continuously passing said accelerated withdrawn portion in a vortical stream through said contact zone;
   (g) solids supply means for continuously introducing a quantity of trichloroisocyanuric acid and isocyanuric acid particulate solids into a central portion of said vortical stream, thereby producing a solids-liquid mixture containing sodium dichloroisocyanurate product; and
   (h) mixed stream feed means for continuously transferring said solids-liquid mixture from said contact zone into said reaction zone.

8. Apparatus for dispersing a dry particulate blend of trichloroisocyanuric acid and isocyanuric acid into a liquid medium containing NaDCC, comprising:
   (a) a vertical funnel having an inner surface;
   (b) a splash guard atop said funnel;
   (c) a liquid medium recycle means, attached to said funnel, for recycling said liquid medium following dispersion of said blend therein;
   (d) a liquid wash means, attached to said funnel, for producing a vortical recycled liquid medium wash stream along said inner surface; and
   (e) braking ridge means, lying along a major portion of said inner surface, for braking said vortical stream.

* * * * *

UNITED STATES PATENT AND TRADEMARK OFFICE
CERTIFICATE OF CORRECTION

PATENT NO. : 4,099,005
DATED : July 4, 1978
INVENTOR(S) : Michael C. Fullington and Kurt H. Moller It is certified that error appears in the above-identified patent and that said Letters Patent are hereby corrected as shown below:

Correct FIGURE 1 to appear as shown below:

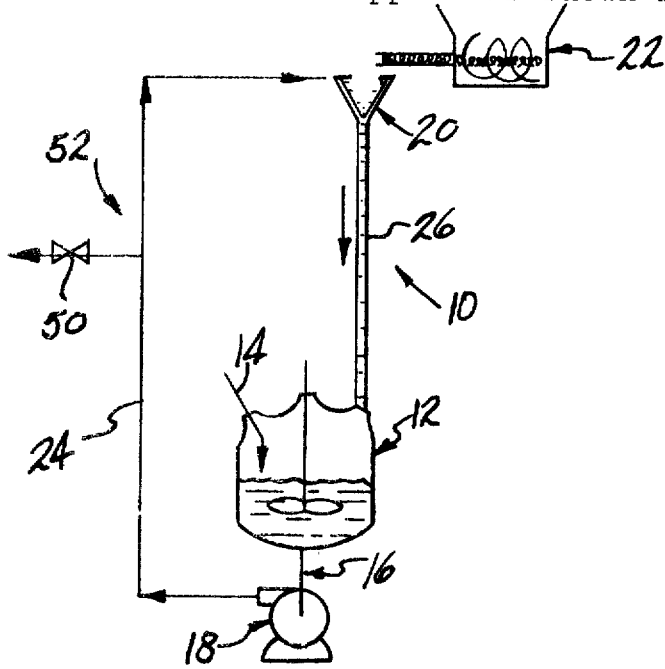

Signed and Sealed this

Thirteenth Day of March 1979

[SEAL]

Attest:

RUTH C. MASON
Attesting Officer

DONALD W. BANNER
Commissioner of Patents and Trademarks